United States Patent
Migliaccio et al.

(10) Patent No.: US 6,960,473 B2
(45) Date of Patent: Nov. 1, 2005

(54) IN VITRO MASS PRODUCTION OF HUMAN ERYTHROID CELLS FROM THE BLOOD OF NORMAL DONORS AND THALASSEMIC PATIENTS

(75) Inventors: Giovanni Migliaccio, Rome (IT); Anna Rita Franco, Rome (IT)

(73) Assignee: Istituto Superiore di Sanita, Rome (IT)

( * ) Notice: Subject to any disclaimer, the term of this patent is extended or adjusted under 35 U.S.C. 154(b) by 0 days.

(21) Appl. No.: 10/786,461

(22) Filed: Feb. 26, 2004

(65) Prior Publication Data

US 2004/0229356 A1 Nov. 18, 2004

Related U.S. Application Data

(60) Provisional application No. 60/449,841, filed on Feb. 27, 2003.

(51) Int. Cl.$^7$ ................................................. C12N 5/08
(52) U.S. Cl. ...................... 435/372; 435/377; 435/378; 435/384; 435/386; 435/387; 435/392
(58) Field of Search ................................. 435/325, 378, 435/383, 384, 386, 387, 392, 372, 377, 404

(56) References Cited

PUBLICATIONS

Migliaccio, Di Pietro, di Giacomo, Di Baldassarre, et al. In vitro mass production of human erythroid cells from the blood of normal donors and of thalassemic patients. Blood, Cells, Molecules, and Diseases. vol. 28, No. 2, pp. 169–180, Mar./Apr. 2002.*
Adcock, I. M. (2001) Glucocorticoid–regulated transcription factors. *Pulm. Pharmacol. Ther.* 14, 211–219.
Bauer, A., Tronche, F., Wessely, O., Kellendonk, C., Reichardt, H. M., Steinlein, P., Schulz, G., and Beug, H. (1999) The glucocorticoid receptor is required for stress erythropoiesis. *Genes Dev.* 13, 2996–3002.
Durand, B., Migliaccio, G., Yee, N. S., Eddleman, K., Huima–Byron, T., Migliaccio, A. R., and Adamson, J. W. (1994) Long–term generation of human mast cells in serum–free cultures of CD34+ cord blood celll stimulated with stem cell factor and interleukin–3. *Blood* 84, 3667–3674.
Fibach, E., Manor, D., Oppenheim, A., and Rachmilewitz, E. A. (1989) Proliferation and maturation of human erythroid progenitors in liquid culture. *Blood* 73, 100–103.
Glaser, V. (1998) Fake blood market gets hemoglobin transfusion from reticulocytes. *Nat. Biotechnol.* 16, 709.
Ikonomi, P., Rivera, C. E., Riordan, M., Washington, G., Schechter, A. N., and Noguchi, C. T. (2000) Overexpression of GATA–2 inhibits erythroid and promotes megakaryocyte differentiation, *Exp. Hematol.* 28, 1423–1431.
Jordan, C. T., and Van Zant, G. (1998) Recent progress in identifying genes regulating hematopoietic stem cell function and fate. *Curr. Opin. Cell Biol.* 10, 716–720.

Kollia, P., Noguchi, C. T., Filbach, E., Loukopoulos, D., and Schechter, A. N. (1997) Modulation of globin gene expression in cultured erythroid precursors derived from normal individuals: Transcriptional and posttranscriptional regulation by hemin. Proc. Assoc. Am. *Physicians* 109, 420–428, abstract only.

Leone, L., Monteleone, M., Gabutti, V., and Amione, C. (1985) Reversed–phase high–performance liquid chromatography of human haemoglobin chains. *J. Chromatogr.* 321, 407–419.

Migliaccio. G., Migliaccio, A. R., Druzin, M. L., Giardina, P. J., Zsebo, K. M., and Adamson, J. W. (1992) Long–term generation of colony–forming cells in liquid culture of CD34+ cord blood cells in the presence of recombinant human stem cell factor. *Blood* 79, 2620–2627.

Migliaccio, A. R., and Papayannopoulou, T. (2001) Erythropoiesis, In Disorders of Hemoglobin (Steinberg, M. H., Forget, B. G., Higgs, D. R., and Nagel, R. L., Eds.), pp. 52–71. Cambridge Univ. Press, Cambridge, UK.

Orkin, S. H., Harosi, F. I., and Leder, P. (1975) Differentiation in erythroleukemic cells and their somatic hybrids. *Proc. Natl. Acad. Sci. USA* 72, 98–102.

Panzenbock, B., Bartunek, P., Mapara, M. Y., and Zenke, M. (1998) Growth and differentiation of human stem cell factor erythropoietin–dependent erythroid progenitor cells in vitro. *Blood* 92, 3658–3668.

(Continued)

*Primary Examiner*—Terry McKelvey
*Assistant Examiner*—Jennifer Dunston
(74) *Attorney, Agent, or Firm*—Rothwell, Figg, Ernst & Manbeck

(57) ABSTRACT

We describe a new two-step culture method for mass production in vitro of erythroid cells from either CD34$^+$ ($10^5$ cells/mL) or light-density ($10^6$ cells/mL) cells purified from the blood of normal donors and thalassemic patients. The method includes (i) culture of the cells in the presence of dexamethasone and estradiol ($10^{-6}$ M each) and (ii) the growth factors SCF (50 ng/mL), IL-3 (1 ng/mL), and EPO (1 U/mL). In their proliferative phase, these cultures generated about $1–2 \times 10^7$ erythroblasts for each milliliter of blood collected from normal donors or thalassemic patients. They were composed mostly (90%) of CD45$^{low}$/glycophorin (GPA)$^{neg}$/CD71$^{low}$ cells at day 7, 50–60% of which became CD45$^{neg}$/GPA+/CD71$^{high}$ by days 15–20. However, when cells from days 7 to 12 of the proliferative phase were transferred in differentiation medium containing EPO and insulin, they progressed to mature erythroblasts (>90% benzidine$^{pos}$ and CD45$^{neg}$/GPA$^+$/CD71$^{medium}$) in 4 days. Because of the high number of erythroid cells that are generated from modest volumes of blood, this method will prove useful in donor-specific studies of erythroid differentiation.

10 Claims, 12 Drawing Sheets

PUBLICATIONS

Papayannopoulou, T., Brice, M., Farrer, D., and Kaushansky, K. (1996) Insights into the cellular mechanisms of erythroprotein–thrombopoietin synergy. *Exp. Hematol. 24*, 660–669.

Piacibello, W., Sanavio, F., Garetto, L., Severino, A., Bergandi, D., Ferrario, J., Fagioli, F., Berger, M., and Aglietta, M. (1997) Extensive amplification and selfrenewal of human primitive hematopoietic stem cells from cord blood. *Blood 89*, 2644–2653.

Rennick, D., Hunte, B., Holland, G., and Thompson–Snipes, L. (1995) Cofactors are essential for stem cell factor–dependent growth and maturation of mast cell progenitors: Comparative effects of interleukin–3 (IL–3), IL–4, IL–10, and fibroblasts. *Blood 85*, 57–65.

Rogers, A., and Eastell, R. (2001) The effect of 17beta–estradiol on production of cytokines in cultures of peripheral blood. *Bone 29*, 30–34.

Stamatoyannopoulos, G., and Grosveld, F. (2001) Hemoglobin switching. In The Molecular Basis of Blood Diseases (Stamatoyannopoulos, G., Majerus, P. W., Perlmutter, R. M., and Varmus, H., Eds.), pp. 135–182. W.B. Saunders Co., Philadelphia.

von Lindern, M., Zauner, W., Mellitzer, G., Steinlein, P., Fritsch, G., Huber, K., Lowenberg, B., and Beug, H. (1999) The glucocorticoid receptor cooperates with the erythropoietin receptor and c–Kit to enhance and sustain proliferation of erythroid progenitors in vitro. *Blood 94*, 550–559.

Ziegler, B. L., Muller, R., Valtieri, M., Lamping, C. P., Thomas, C. A., Gabbianelli, M., Giesert, C., Buhring, H. J., Kanz, L., and Peschle, C. (1999) Unicellular –unilineage erythropoietic cultures: Molecular analysis of regulatory gene expression at sibling cell level. *Blood 93*, 3355–3368.

* cited by examiner

IN VITRO MASS PRODUCTION OF HUMAN ERYTHROID CELLS FROM THE BLOOD OF NORMAL DONORS AND THALASSEMIC PATIENTS

BACKGROUND OF THE INVENTION

Most of the biochemical studies on the characterization of erythroid cells, which require a mass number of cells, were and still are performed using cell lines as a model. This is exemplified by the studies on the regulation of globin gene expression that have highly relied on the use of the murine MEL cells and the human K562, HEL, and UT-7 cell lines (G. Stamatoyannopoulos, et al., The Molecular Basis of Blood Diseases, 135 (2001)) of primary cells, as many regulatory pathways have been altered during the transformation process that led to their immortalization. Therefore, investigators have tried to establish in vitro unilineage differentiation of primary erythroid cells to be used as a model in those studies (V. Glaser, Nat. Biotechnol. 16, 709 (1998)). Homogeneous populations of primary human erythroid cells through unilineage-specific culture conditions have relied on the use of progenitor ($CD34^+$) cells purified from neonatal blood or from adult marrow and cultured in the presence of stimulators of the glucocorticoid receptor, such as dexamethasone (B. Panzenbock, et al. Blood 92, 3658–3668 (1998); M. von Lindern, et al. Blood 94, 550–559 (1999)). This method allows up to one-thousand-fold amplification of differentiated cells. However, for practical and ethical reasons, it is not always possible to obtain specimens with a number of cells sufficient for $CD34^+$ selection from a specific donor. Conversely, it is well known that the behavior in culture of primary cells reflects the genomic heterogeneity of the donor from whom they are derived (C. T. Jordan et al., Curr. Opin. Cell Biol. 10, 716–720). There are many cases in which unilineage differentiation from a specific donor would allow an estimate of the influence of a particular genetic background on the response being studied. In these cases, it may not be ethically appropriate to harvest marrow or blood from the patient in amounts sufficient for $CD34^+$ cell purification. Unilineage differentiation of erythroid cells has been achieved, starting with light-density cells purified from the blood with a two-step culture method that physically separates the stimulation of the cells with growth factors, allowing commitment with those required for the maturation of erythroid cells (E. Fibach et al., Blood 73, 100 (1989)). However, the amplification obtained with such a technique is very modest and does not allow mass cell production. Herein is a description of a new two-phase culture method that allows mass production of primary human erythroid cells, starting from the light-density cells of normal donors and thalassemic patients. In both cases, highly homogeneous primary erythroid cells are produced in numbers sufficient for biochemical and molecular studies from very modest volumes (10 mL) of blood. Therefore, this method will be useful for donorspecific studies of hemoglobin F reactivation, to identify inducers targeted for each specific patient.

SUMMARY OF INVENTION

The present invention provides a new two-phase culture method that allows mass production of primary human red cells, starting from the mononuclear blood cell fraction of normal and thalassemic individuals. In this method, designed on the basis of results presented on erythroid cell production from $CD34^+$ cells (FIGS. 1 and 2), light-density cells are first cultured with an optimal concentration of SCF and EPO, and very low ($\frac{1}{10}$ of the optimal) concentrations of IL-3, dexamethasone and estradiol (proliferative phase). Anytime from 8 to 14 days of culture, the cells are harvested and their terminal differentiation induced with EPO and insulin (differentiative phase).

Therefore, a first object of the present invention is a method of producing primary human erythroid cells comprising the steps of (i) obtaining light-density cells from a blood sample, (ii) culturing these light-density cells in a first culture medium comprising stem cell factor, erythropoietin, interleukin-3, dexamethasone and estradiol, thereby obtaining proliferation of the cells, and (iii) re-culturing these cells in a second culture medium comprising erythropoietin and human insulin, thereby obtaining differentiation of the cells into primary human erythroid cells.

Further, a second object of a method of producing primary human erythroid cells comprising the steps of (i) obtaining light-density cells from a blood sample, (ii) culturing these light-density cells in a first culture medium comprising stem all factor, erythropoietin, interleukin-3, dexamethasone and estradiol, thereby obtaining proliferation of the cells, (iii) washing the cells, and (iv) re-culturing these cells in a second culture medium comprising erythropoietin and human insulin, thereby obtaining differentiation of the cells into primary human erythroid cells.

These methods allow for obtaining approximately $1-2\times 10^7$ erythroblasts for each milliliter of blood collected from normal donors or thalassemic patients. As it is feasible to determine hemoglobin synthesis on these cells with as few as $3\times 10^5$ cells (FIG. 11), it is possible, with minimum discomfort for the donor, to identify in vitro HbF inducers targeted for each specific patient and to determine their most effective concentration.

DETAILED DESCRIPTION OF THE INVENTION

Figure 1:
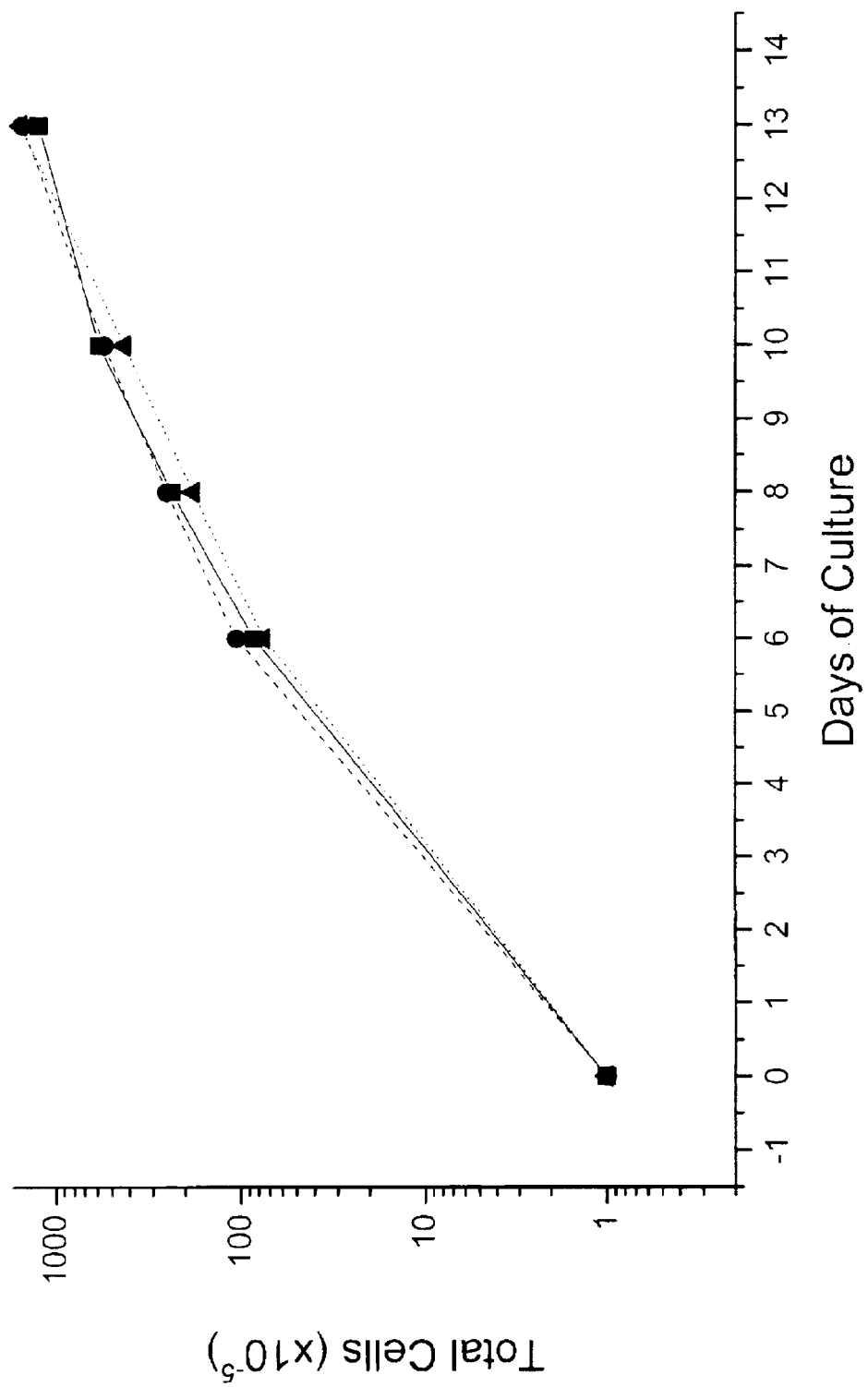
FIG. 1. Total cell number in liquid culture of normal adult $CD34^+$ cells stimulated with a combination of growth factors including SCF, IL-3, and EPO (straight lines) or with the further addition of estradiol (dashed lines) or dexamethasone (dotted lines). Identical cell amplifications were obtained under the three conditions. One representative experiment is presented. Similar results were obtained in two additional cultures.

Our knowledge of the physiology of normal erythroid cells has greatly improved, thanks to the development of culture conditions allowing their synchronous differentiation in vitro free from contaminating cells. This "unilineage" cell differentiation was made possible by the cloning of SCF. Human $CD34^+$ cells purified from various sources undergo massive multi-lineage differentiation under serum-deprived culture conditions stimulated with the combination of SCF, IL-3 and one of the lineage-specific growth factors, either EPO, granulocyte-colony stimulating factor (GCSF) or thrombopoietin (TPO) (G. Migliaccio, et al., Blood 79, 2620–2627 (1992); W. Piacibello, Blood 89, 2644–1653 (1997)). However, as soon as IL-3 is omitted from the cultures, the differentiation observed is unilineage and, depending on the growth factor that complements SCF, is erythroid, granulocytic or megakaryocytic. However, the purity of the differentiated cells is obtained at the expense of the number of cells amplified, which is barely sufficient for simple molecular biology experiments such as gene expression analysis (B. L. Ziegler, et al., Blood 93, 3355–3368 (1999)). The problem of the low number of cells obtained in unilineage cell cultures was solved by adding to the "cocktail" of SCF and EPO factors that stimulate the glucocorticoid receptor, such as dexamethasone (B. Panzenbock, et al. Blood 92, 3658–3668 (1998); M. von Lindern, et al. Blood 94, 550–559 (1999)). The glucocorticoid receptor is necessary for the response to acute erythroid stimulation, because mice in which the receptor has been knocked down by homologous recombination have a normal hematocrit, but do not recover from phenyl-hydrazine-induced hemolytic anemia (A. Bauer, Genes Dev. 13, 2996–3002 (1999)). In vitro stimulation of the erythroid cells with dexamethasone inhibits their differentiation, allowing them to proliferate for longer time (M. von Lindern, et al. Blood 94, 550–559 (1999)). The number of erythroid cells obtained at the end of the culture period from $CD34^+$ cells is sufficient for more sophisticated molecular analysis, such as transient gene expression studies (P. Kollia, et al. Proc. Assoc. Am. Physicians 109, 420–428 (1997); P. Ikonomi et al., Ep. Hematol. 29, 1423–1431 (2000)). However, this method relies on the use of high numbers of $CD34^+$ cells and therefore on the availability of large human specimens. The principle of massive unilineage differentiation is to allow differentiation of progenitors cells under conditions that only permit survival of cells of the appropriate lineage. The differentiation stimuli applied to the system, however, must not be so strong that all the cells differentiate at the expense of their proliferation. A problem encountered when light-density cells are used as a target is that the lymphocytes and the monocytes present in the sample will soon release growth factors which, in turn, will allow survival of cells for other lineages. A further problem is represented by the fact that IL-3 synergizes with SCF, both for proliferation of all the hemopoietic cells (G. Migliaccio, Blood 79, 2620–2627 (1992)) and for mast cell differentiation (B. Durand et al., Blood 84, 3667–3674 (1994); D. Rennick, Blood 85, 57–65 (1995)). Therefore, when IL-3 is added to the culture, the total number of cells produced is higher, but those are contaminated with mast cells.

Figure 2:
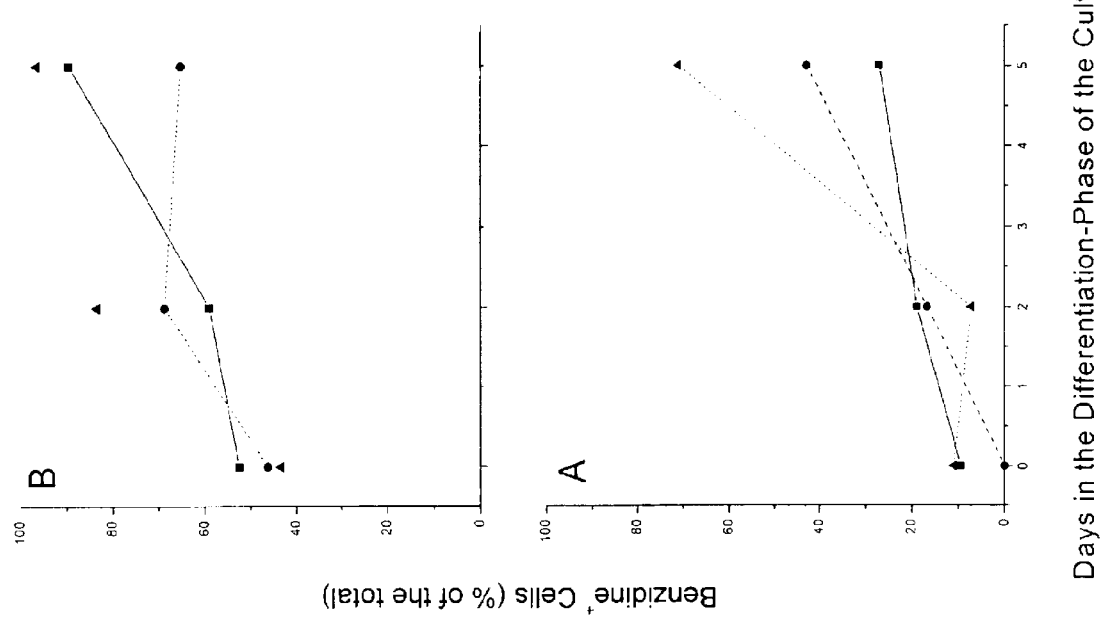
FIG. 2. Frequency of benzidinepos cells in cultures of cells harvested either at day 8 (A) or 13 (B) from the cultures shown in FIG. 1 and induced to differentiate for 5 additional days in the presence of EPO and insulin. Results obtained with cells, which had been previously cultured with growth factors alone or with growth factors supplemented with estradiol or with dexamethasone, are indicated by straight, dashed and dotted lines, respectively. The data at day 0 in this figure provide the frequency of benzidinepos cells at days 8 (A) and 13 (B) of the original cultures presented in FIG. 1. One representative experiment, of three independent cultures performed, is presented.
Figure 3:
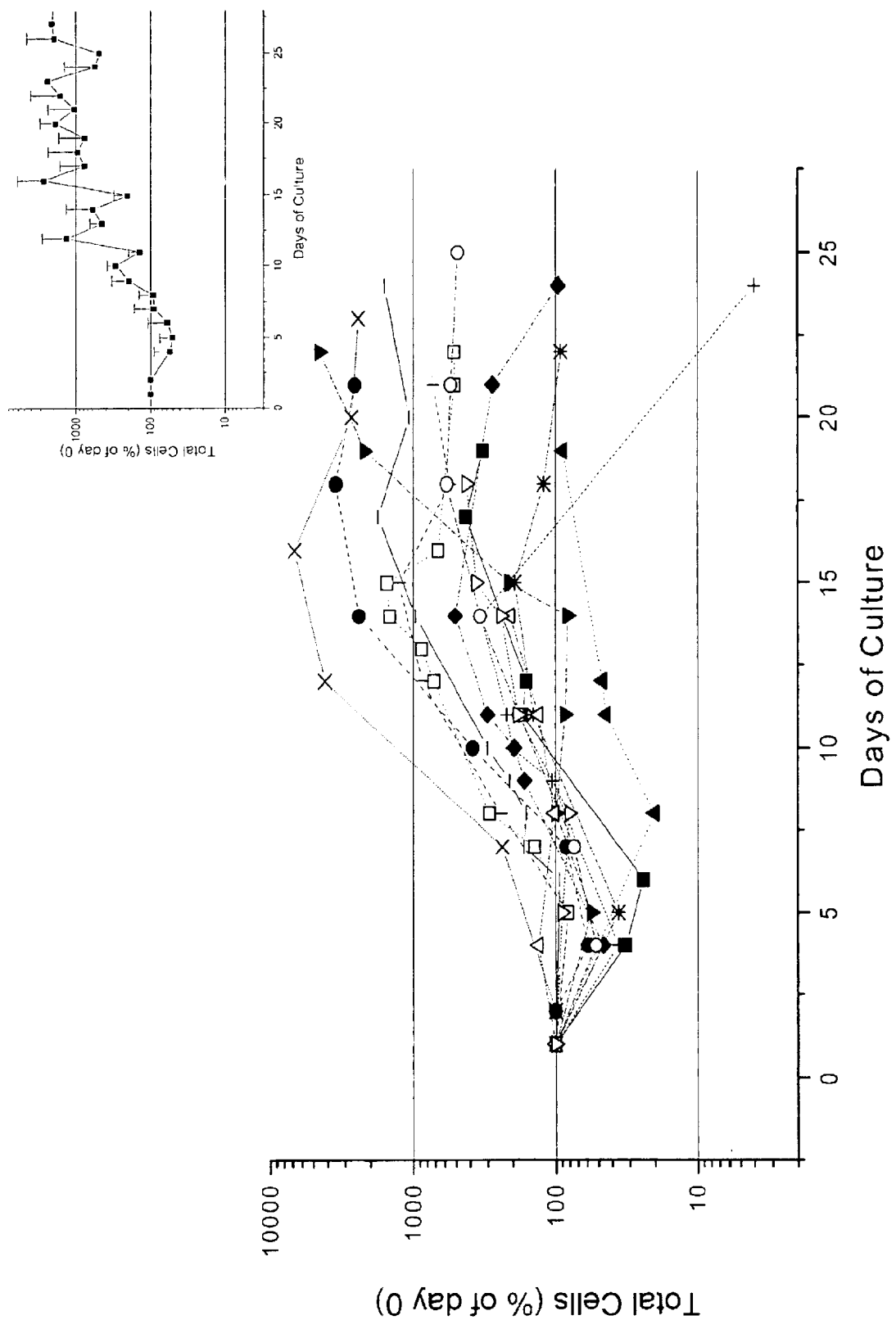
FIG. 3. Total cell number (in percentage of the input values) observed in cultures of light-density cells purified from the blood of normal donors (13 different donors, each symbol a different individual) stimulated with SCF, IL-3, and EPO plus estradiol plus dexamethasone. In all of the cases, the cultures were started with 106 light-density cells per milliliter. Means (±SD) of the values obtained in all experiments performed are presented in the inset.
Figure 4:
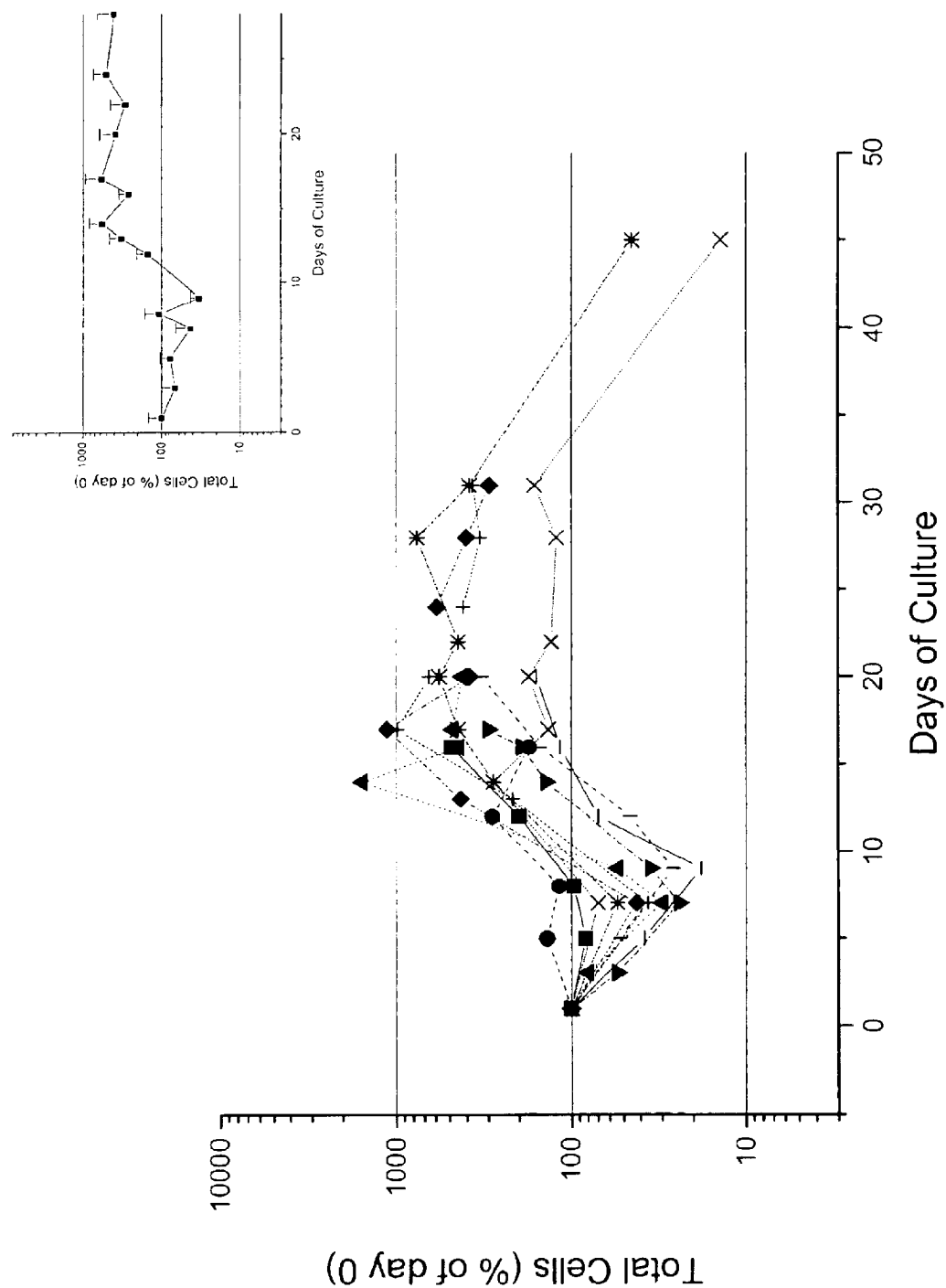
FIG. 4. Total cell number (in percentage of the input values) observed in cultures of light-density cells purified from the blood of thalassemic patients (10 different donors, each symbol a different donor) stimulated with SCF, IL-3 and EPO plus estradiol plus dexamethasone. In all of the cases, the cultures were started with $10^6$ light-density cells per milliliter. Means (±SD) of the values obtained in all the experiments are presented in the inset.
Figure 5:
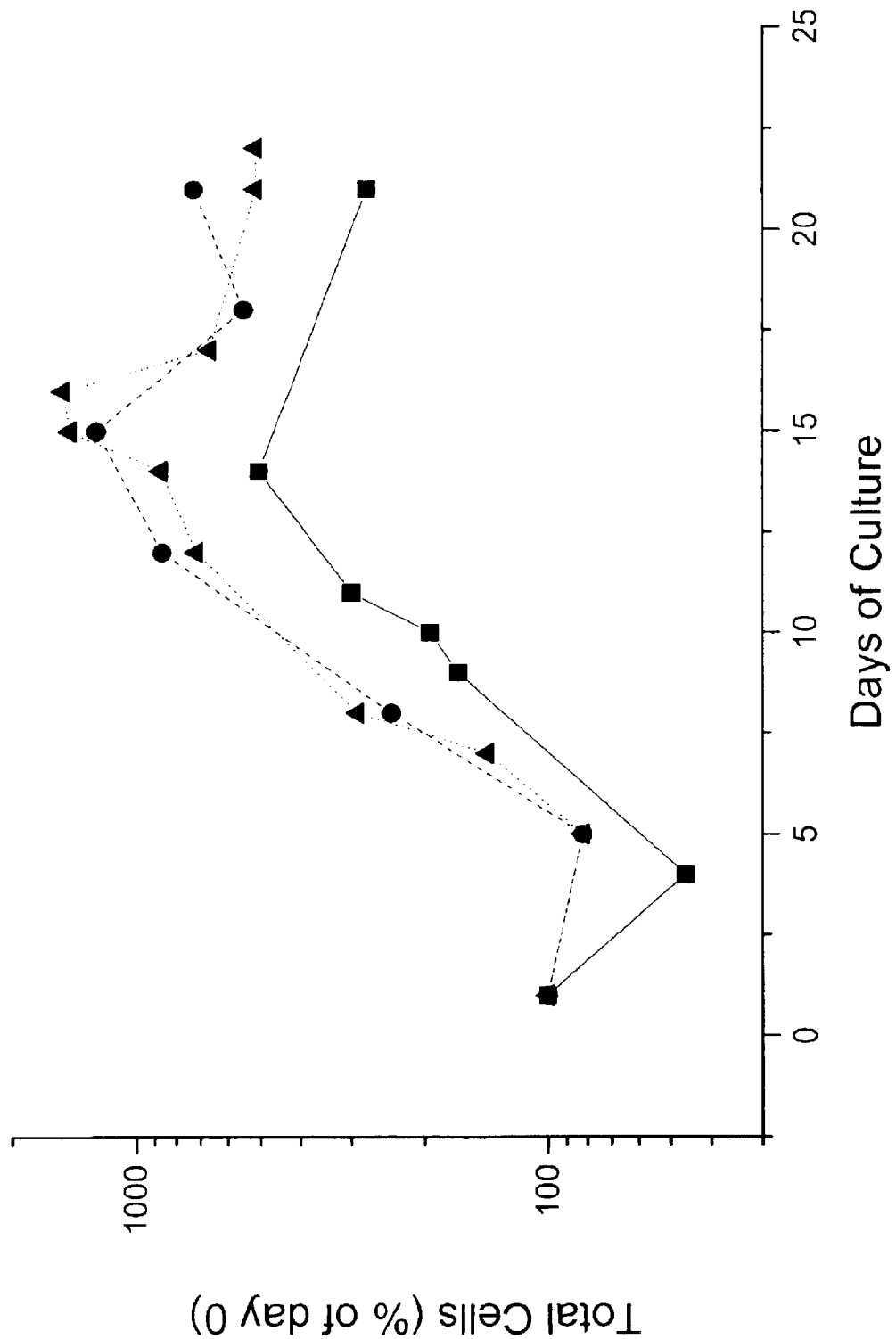
FIG. 5. Total cell number observed in three replicate cultures of light-density cells purified from the blood of the same normal donor stimulated with SCF, IL-3 and EPO plus estradiol plus dexamethasone.
Figure 6:
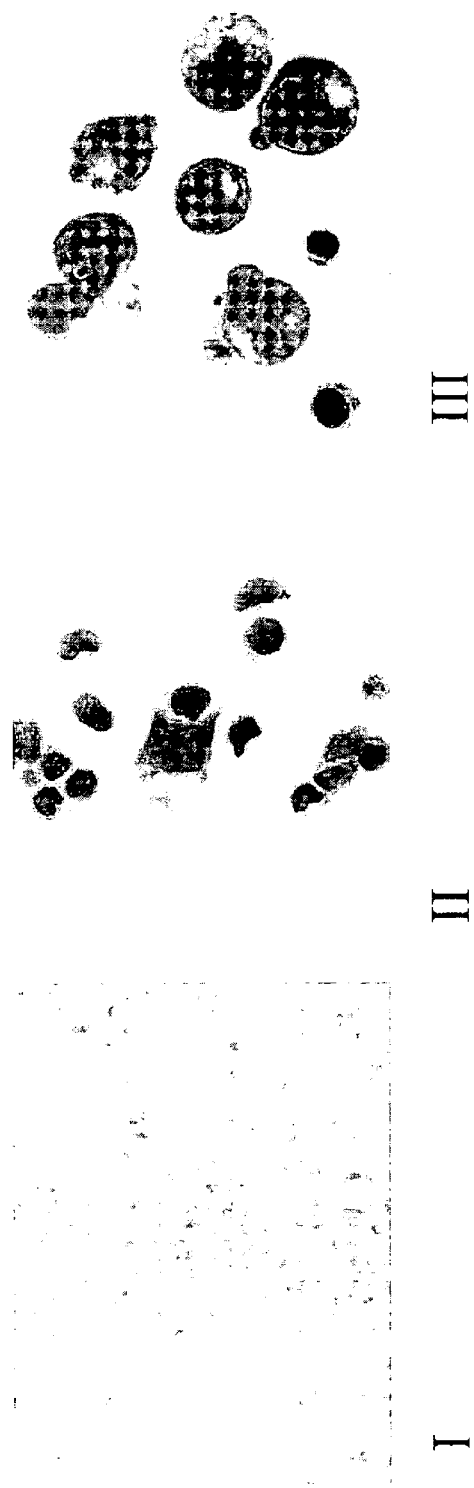
FIG. 6. Photograph of the cells in a representative proliferative cell culture (I) and May-Grunwald staining of cytocentrifuged preparations of cells obtained at day 7 (II) and day 16 (III) from the same culture (magnification: 10× in I and 100× in II and III, respectively).
Figure 8:
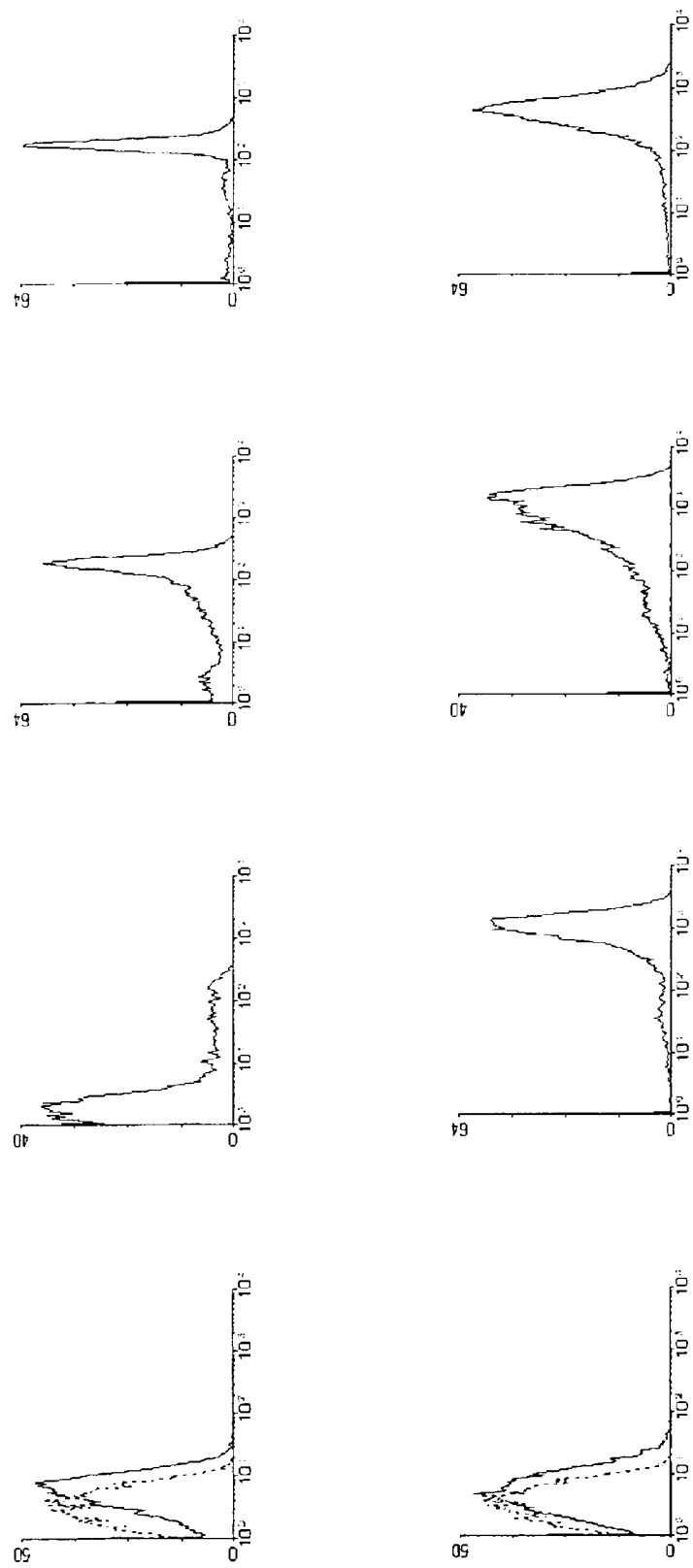
FIG. 8. Flow cytometry analysis for the expression of glycophorin A (top) and CD71 (bottom) in cells obtained at days 0, 7, 12, and 16 from a representative culture of light-density cells purified from a normal donor and stimulated with SCF, IL-3, EPO, estradiol, and dexamethasone.
Figure 9:
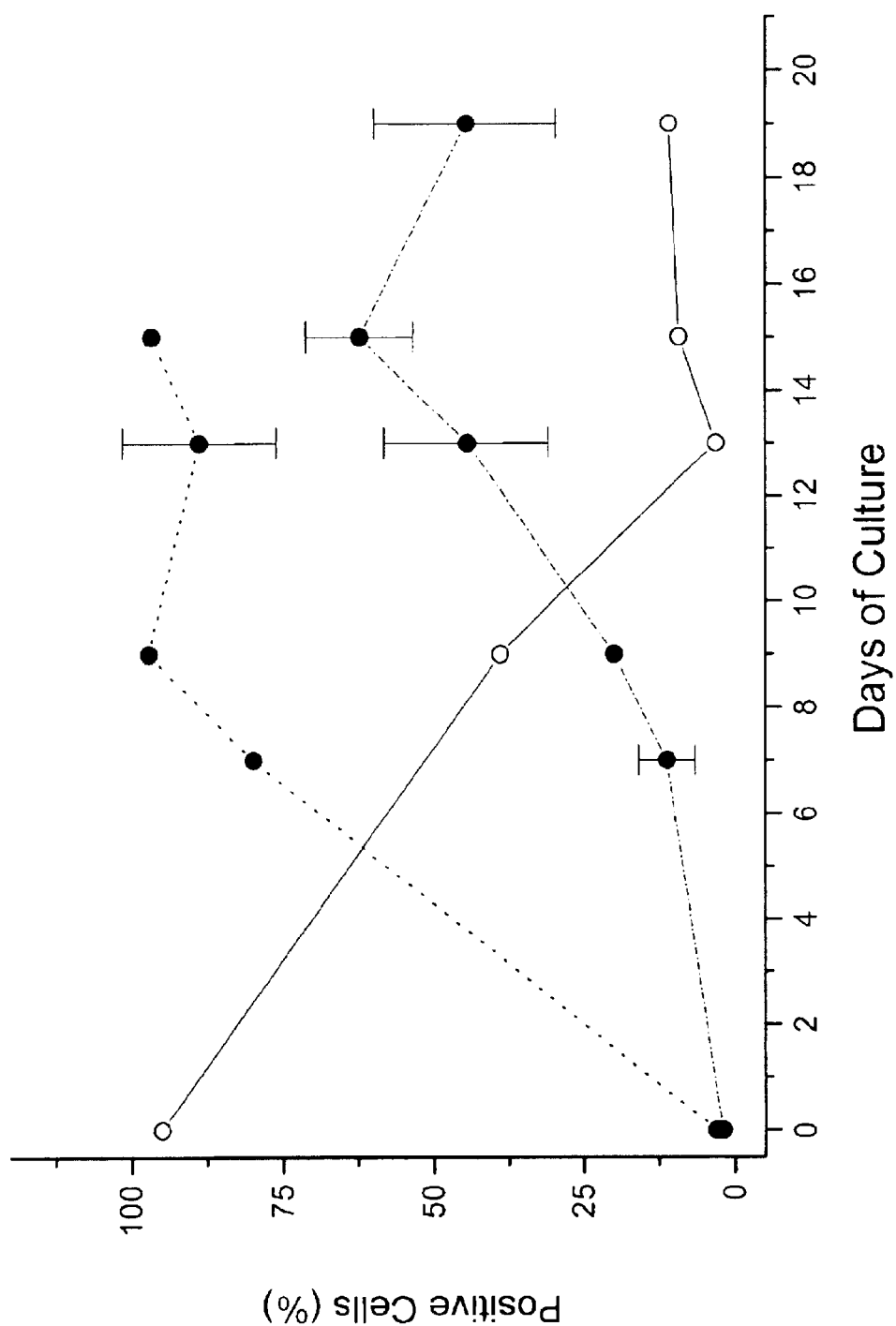
FIG. 9. Frequency of $CD45^+$ (straight lines), $CD71^+$ (dotted lines), and glycophorin $A^+$ (dash-and-dot lines) cells in culture of light-density cells purified from normal donors and stimulated with SCF, IL-3, EPO, estradiol, and dexamethasone. Results are presented as means (±SD) of 5–10 replicate cultures. When SDs are not shown, results are from one representative experiment.
Figure 10:
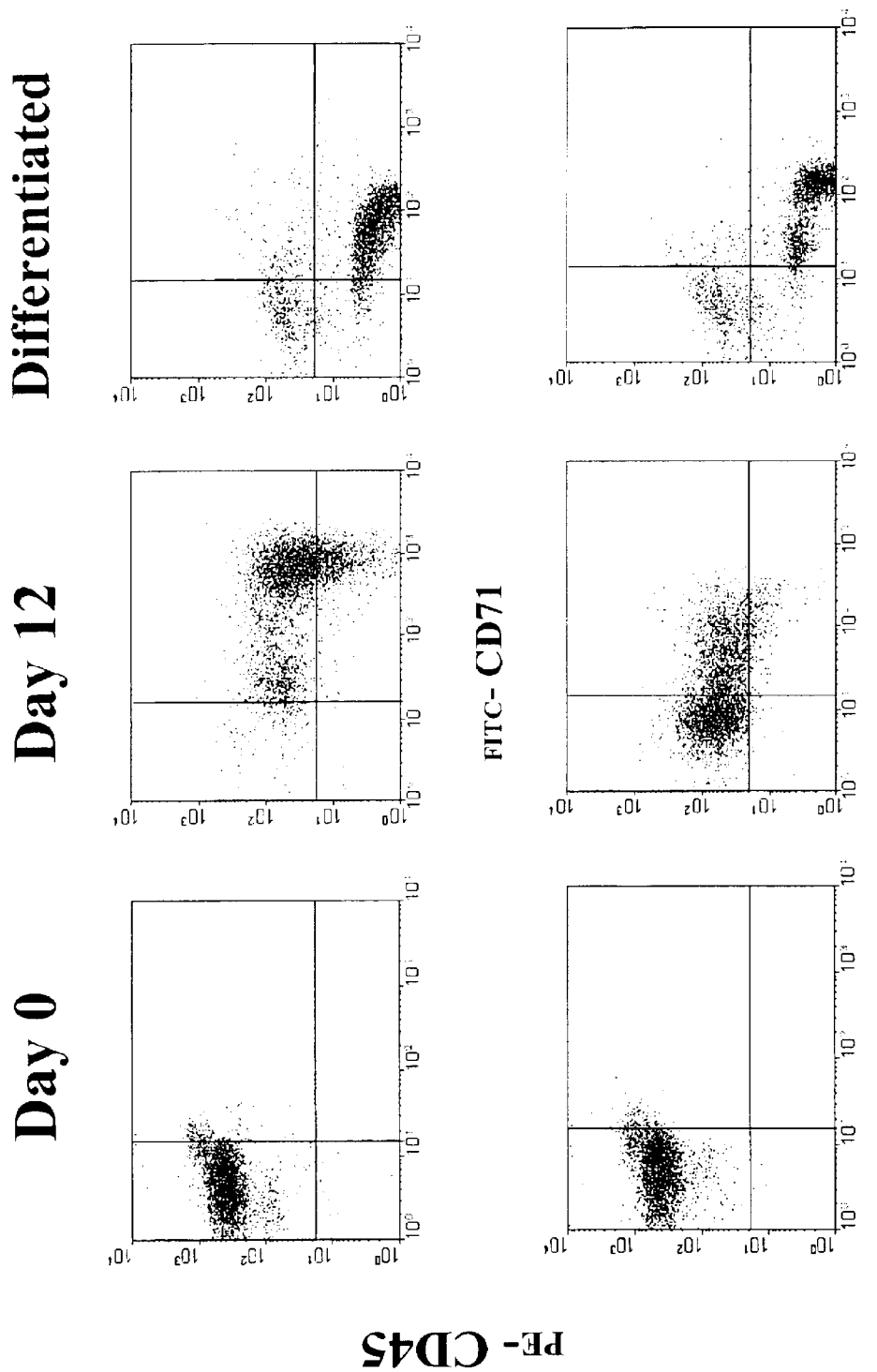
FIG. 10. Flow cytometry analysis for the coexpression of CD45 and CD71 (top) and CD45 and glycophorin A (bottom) of light-density mononuclear cells purified from a normal donor (on the left) and of the same cells cultured for 12 days in the presence of all growth factors plus dexamethasone and estradiol (middle panels) or for 8 days in these conditions plus 4 additional days in the presence of EPO and insulin (differentiated, on the right).

The present invention provides a new two-phase culture method that allows mass production of primary human red cells, starting from the mononuclear blood cell fraction of normal and thalassemic individuals. In this method, designed on the basis of results presented on erythroid cell production from $CD34^+$ cells (FIGS. 1 and 2), light-density cells are first cultured in a first culture medium with an optimal concentration of SCF and EPO, and very low (1/10 of the optimal) concentrations of IL-3, dexamethasone and estradiol (proliferative phase). Preferably the first culture medium is supplemented with 10 ng/ml SCF, 1 u/ml EPO, 1 ng/ml IL-3, $10^{-6}$ M dexamethasone and $10^{-6}$ M estradiol. Dexamethasone not only favors erythroid cell proliferation (M. von Lindern, et al., Blood 94, 550–559 (1999)), but also inhibits activation of T cells (I. M. Adcock, Pulm. Pharmacol. Ther. 14, 211–219 (2001)), while estradiol may inhibit growth factor production from the monocytes (A. Rogers et al., Bone 29, 30–34 (2001)) Anytime from 8 to 14 days of culture, the cells are harvested and their terminal differentiation induced in a second culture medium with EPO and insulin (differentiative phase). Preferably, the second cell culture is supplemented with 1 u/ml EPO and 10 ng/ml human recombinant insulin. The cell culture medium may be any appropriate culture medium for culturing light-density cells from a blood sample. Preferably the culture medium is IMDM with 20% fetal bovine serum as the first culture medium, and IMDM with 20% fetal calf serum as the second culture medium. In proliferative cultures of cells from both normal donors and thalassemic patients, there was an early (days 2–7) reduction in cell number concomitant with the disappearance of the lymphoid cells and followed by an increase in total cell number that reached a peak around days 10–15 (FIGS. 3 and 4). The variability in the kinetics of amplification observed is probably ascribed to donor-related differences in response to the culture conditions than to conditions themselves. In fact, three separate cultures, using cells from the same donor, gave consistently similar kinetics of expansion (FIG. 5). In most of the experiments, the majority of the cells present at day 10 of the proliferative phase were erythroblasts at different stages of maturation, which eventually terminally differentiate by days 16–18 (FIGS. 6–9). In a few cases, there was a significant monocyte contamination by day 8 (FIG. 7B) that was followed by the progressive appearance of mast cells toward day 20 of culture. The presence of these contaminants was donor-related and could be due to IL-3 hypersensitivity of the cells from these subjects. In any case, whenever the cells in the proliferative phase were harvested between days 8 and 12, washed and re-cultured in the differentiative phase, they generated a homogeneous population of mature erythroid cells in 4 days (FIG. 10). The terminal maturation was similarly efficient, even when the cells had been cryopreserved for an extended period of time before differentiation was induced. This fact represents an important advantage in biochemical studies, because it would allow repeated assays on the same cell population from the same individual. This method allows to obtain approximately $1-2\times10^7$ erythroblasts for each milliliter of blood collected from normal donors or thalassemic patients. As it is feasible to determine hemoglobin synthesis on these cells with as few as $3\times10^5$ cells (FIG. 11), it is possible, with minimum discomfort for the donor, to identify in vitro HbF inducers targeted for each specific patient and to determine their most effective concentration.

However, it should be noted that although the total cell amplification in this system is only 10- to 20-fold, when the efficiency of the CD34 purification and the number of cells obtained at the end of the cultures are taken into account, they are comparable with those obtained with the 1000-fold amplification observed with CD34$^+$ cells. The high number of erythroid cells obtained with this method and their homogeneity make it possible to perform, during the 4 days of the differentiation phase, a series of different biochemical studies including signal transduction analysis and transient gene expression and transactivation experiments of reporter genes, to identify erythroid-specific mechanisms, etc. In conclusion, this is a new two-phase culture method that allows mass production of primary human red cells starting from the mononuclear blood cell fraction of normal donors and thalassemic patients. The erythroid cells are produced in sufficient numbers for biochemical and molecular studies and may provide a model to study erythroid-specific processes.

EXAMPLES

Human Subjects

Normal blood buffy coats were obtained from the Italian Red Cross Blood Bank in Rome. Blood from homozygote β°-thalassemic patients was collected before its routine transfusion at the Center for Studies on Thalassemia, University of Cagliari, and shipped via overnight delivery to Rome for further analysis. In both cases, collection of human samples was done according to the guidelines established by the local ethical committee for human subject studies.

Cell Purification

Mononuclear cells were separated by centrifugation at 400 g×30' over Ficoll-Hypaque (Amersham-Pharmacia Biotec, Uppsala, Sweden). Light-density cells were collected, washed with Hank's basal salt solution supplemented with 1% (w/v) bovine serum albumin, and either cultured directly or cryopreserved in 10% dimethyl sulfoxide (Sigma, St. Louis, Mo.). Frozen cadaveric marrow cells obtained from Northwest Tissue Center, Puget Sound Blood Bank (Seattle, Wash.) were thawed, washed, and incubated overnight in IMDM with 10% fetal calf serum on tissue culture plates to remove adherent cells. From the nonadherent cells, CD34$^+$ cells were isolated by direct immunoadherence on anti-CD34 monoclonal antibody (T. Papayannopoulou et al., Exp. Hematol. 24, 660–669 (1996)).

Cell Culture

Light-density cells and CD34$^+$ cells were cultured for the proliferative phase in Iscove's modified Dulbecco's medium (IMDM, Mascia Brunelli, Milan, Italy) containing 20% of fetal bovine serum (FBS, Hyclone, Logan, Utah) and supplemented with Stem Cell Factor (SCF, 10 ng/mL) (Amgen, Thousand Oaks, Calif.), Erythropoietin (EPO, 1 u/mL) (Epoetina alfa, Dompe Biotec, Milan, Italy), Interleukin-3 (IL-3, 1 ng/mL) (Bouty, Milan, Italy), dexamethasone ($10^{-6}$ M) (Sigma), and estradiol ($10^{-6}$ M) (Sigma). Light-density and CD34$^+$ cells were seeded at a concentration of $10^6$ and $10^5$ cells/mL, respectively. In both cases, the cultures were diluted over time with as much fresh medium, as necessary, to maintain the cell concentration in the range of $1-2\times10^6$ cells/mL. To induce differentiation, the cells were harvested from the culture, washed with IMDM, and cultured in fresh IMDM in the presence of 20% FCS, EPO (1 u/mL) and human recombinant insulin (10 ng/mL) (Calbiochem, Darmstadt, Germany).

Phenotypic Analysis of the Cells

Cell morphology was analyzed according to standard criteria on cytocentrifuged (Shandon, Astmoor, England) smears stained with May-Grumwald-Giemsa. Hemoglobin-containing cells were identified by benzidine staining (S. H. Orkin, Proc. Natl. Acad. Sci. USA 72, 98–102 (1975)). The cell antigenic profile was analyzed by flow cytometry with a Coulter Elite ESP Cell Sorter (Coulter, Miami, Fla.) according to standard protocols. Cells were briefly resuspended in Ca$^{2+}$ and Mg$^{2+}$-free phosphate-buffered saline (PBS) supplemented with 1% (v/v) bovine serum albumin, 2 mM EDTA and 0.01% NaN$_3$, and labeled on ice with phycoerythrin (PE)-conjugated CD45 and fluorescein isothiocyanate (FITC)-conjugated CD71 and anti-glycophorin A (Immunotech, Beckmann-Coulter, Milan, Italy). Cells incubated with the corresponding, irrelevant, isotype-matched antibodies were used for gating nonspecific fluorescence and dead cells were excluded by propidium iodide staining (5 µg/mL) (Sigma).

HPLC for Globin-Chain Analysis

Globin-chain biosynthesis was determined in mature erythroid cells ($3\times10^5$) incubated with [$^3$H]leucine (TRK 754, Amersham Biotech). Cell lysates were subjected to RP-HPLC, as described (L. Leone, et al., J. Chromatogr. 321, 407–419 (1985)). The analytical system used for globin chain separation was HPLC System Gold Beckman, Bio-Rad Lichrospher RP8, 5-m beads, 250×4 mm, and the Bio-Rad 2128 fraction collector. Mobile phase was prepared using acetonitrile, methanol and 0.155 M NaCl (acidified to pH 2.7 with HCl). Eluent A and Eluent B were in the proportion of 50:20:30 and 25:40:35, respectively. A linear gradient from 90 to 20% of solvent B was applied for 95 min, at a flow rate of 0.7 mL/min. Peaks were identified by comparing their retention times with those of peaks obtained from known hemoglobin solutions. This method allows quantification of the relative amounts of each chain by peak area measurement. Collected fractions (350 µl) from heme to globin chain were counted in their elution order in a scintillation counter and plotted cpm count in a scale vs elution time.

Effects of Estradiol and Dexamethasone in Liquid Cultures of CD34$^+$ Cells Purified from Normal Donors The total cell number observed in cultures of CD34$^+$ cells cultured for up to 14 days in the presence of the combination of SCF, IL-3 and EPO (growth factors, GFs), alone or with the further addition of estradiol or of dexamethasone, is presented in FIG. 1. In all three conditions analyzed, the total cell number per culture rose from $0.1\times10^6$ cells at day 0 to $10\times10^6$ at day 7 and continued to increase, reaching up to $100\times10^6$ by day 13. After benzidine staining (mature erythroid cells) in cultures stimulated with GFs alone, the percent of positive cells rose from as few as 10% at day 8 to about 50% at day 13 (see day 0 in FIG. 2). In the other two cases, the benzidinepos cells were either undetectable (GFs plus estradiol) or <10% (GFs plus dexamethasone), rising up to 40% by day 13 (FIG. 2). Since the large increase in total cell number observed in these cultures was associated with modest accumulation of differentiated cells, they were termed proliferative-phase cell cultures. At days 8 and 13 of the proliferative phase, the cells were harvested and cultured for an additional 5 days in fresh medium stimulated with EPO and insulin (FIG. 2). Under those conditions, only modest cell proliferation was observed, with the total number of cells doubling by day 2 and returning to input levels by day 5. At the same time, the frequency of benzidine$^{pos}$ cells increased over time, although the magnitude of the increase was dependent on factors that the cells had been exposed to in the proliferative phase. Cells exposed to GFs alone became 20 or 80% benzidine$^{pos}$, depending on whether they had been primed for 8 or 13 days, respectively (FIG. 2). Cells that had been exposed to GFs plus dexamethasone or to GFs plus estradiol reached the same frequency of benzidine$^{pos}$ cells (80–95 or 40–60%, respectively), independently from the duration of the priming in the proliferative phase (either 8 or 13 days). Since, in the EPO-plus-insulin cultures, the modest increase in cell number was associated with a consistent increase in the frequency of benzidinepos cells, these cultures represented the differentiative-phase cell culture. The total number of erythroid cells obtained at the end of the proliferative-plus-differentiative phase can be calculated by multiplying the total number of cells presented in FIG. 1 by the frequency of benzidine$_{pos}$ cells presented in FIG. 2. When the differentiation was started with cells at day 8 of the proliferative phase, up to $2\times10^6$ vs $7\times10^6$ erythroid cells were obtained in cultures stimulated with GFs alone or supplemented with GFs plus dexamethasone. When the differentiation was started with cells at day 13 of the proliferative phase, as many as $80\times10^6$ were obtained, starting with an input value as low as $10^5$ CD34$^+$ cells.

Figure 7A:
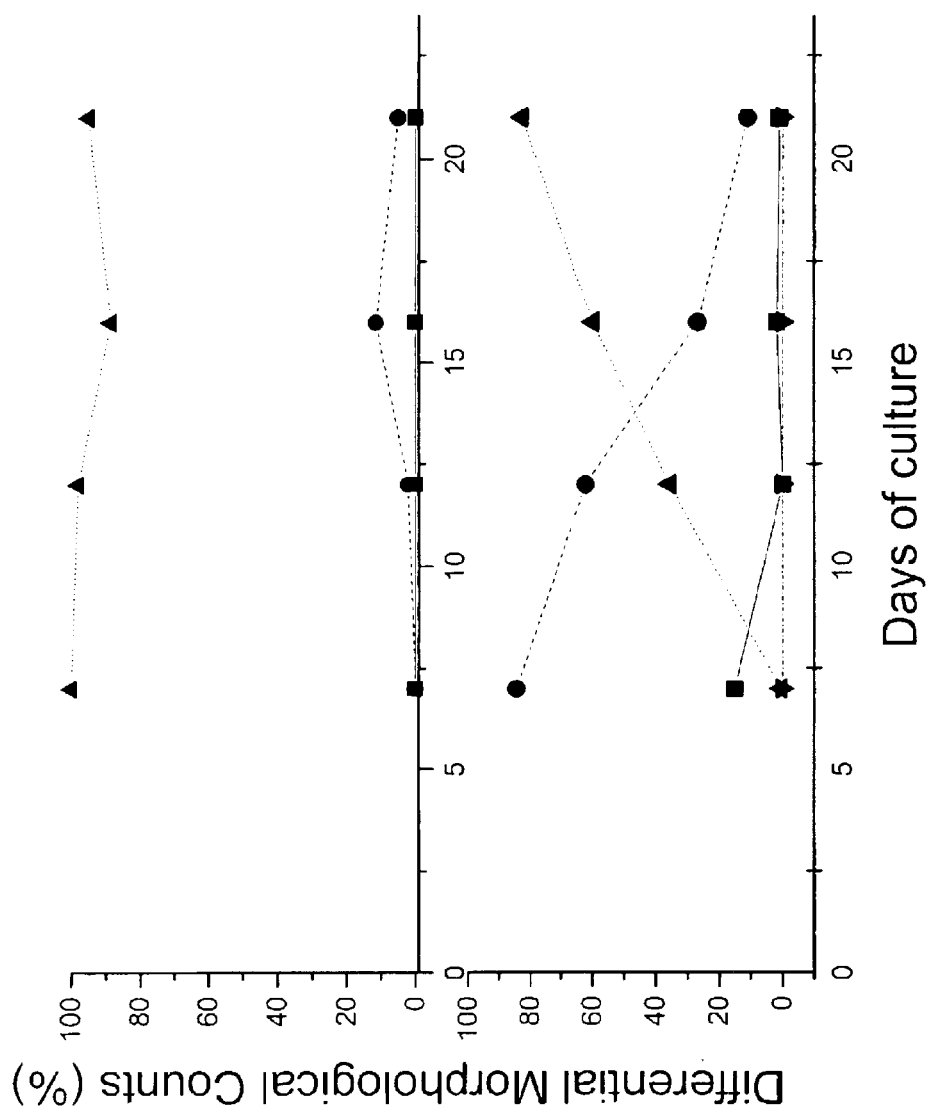
FIG. 7. (A, B) Differential morphological counts of May-Grunwald-Giemsa-stained cytocentrifuged smears of cells obtained from proliferative phase-cultures of light-density cells from two different normal donors. The top panels present the relative frequency of lymphoid (straight line), monocytic (dashed line) and erythroid cells (dotted line), while the lower panels present the relative frequency of erythroid blasts (straight line), of immature (pro- and basophilic erythroblasts) (dashed line) and mature (polychromatophil and orthochromatic erythroblasts) (dotted line) erythroid cells, and of reticulocytes (dashed dot line). During the study, two differentiation behaviors were observed whose extreme cases are presented in A and B, respectively. In the case presented in A, very few monocytic cells were detected in the culture up to 21 days and the majority of the cells (>95%) were erythroblasts at all stage of maturation. However, no reticulocytes were ever observed. In the second case (B), the frequency of monocytes progressively increased in time to reach a frequency of 30% the cells at day 16 when reticulocytes were also detected on the smear.
Figure 7B:
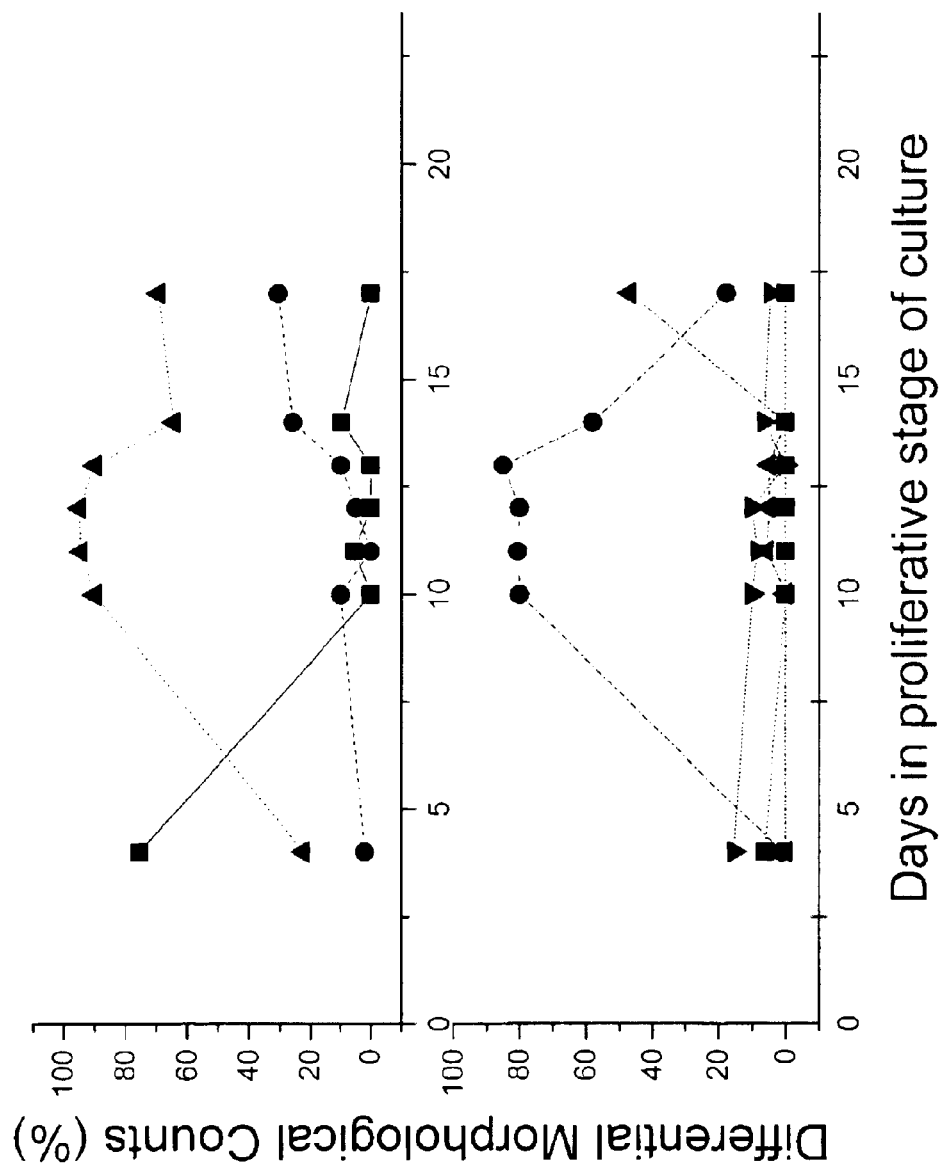
Figure 11:
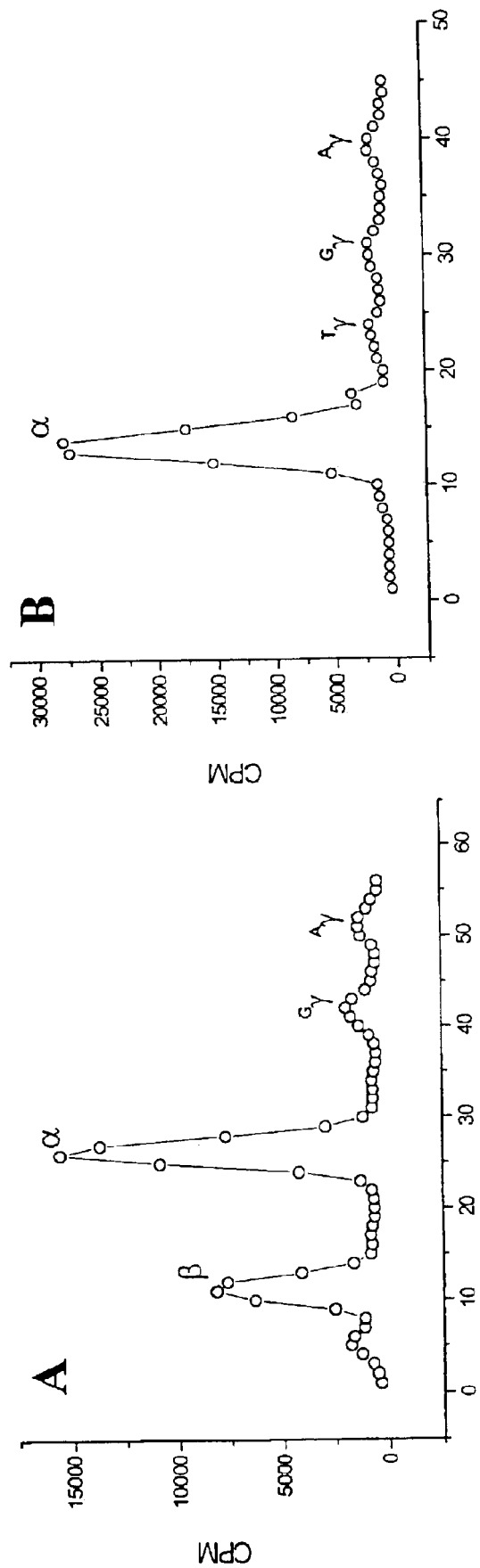
FIG. 11. HPLC separation profiles of globin chains present in erythroid cells obtained after 8 days of culture in proliferative phase followed by 3 additional days of culture in differentiative phase. The cultures were started with light-density cells purified either from a normal volunteer (A) or from a thalassemic patient (B).

Mass Production of Erythroid Cells from the Light-Density Fraction of Blood from Normal Donors and Thalassemic Patients On the basis of the data obtained with CD34$^+$ cells, a culture strategy was devised for mass production of erythroid cells, starting from the light-density cells purified from blood of normal donors and thalassemic patients. This strategy included the culture of the cells for up to 25 days in the presence of GFs plus estradiol and dexamethasone. The total cell numbers observed in the cultures started with either normal or thalassemic light-density cells are presented in FIGS. 3 and 4, respectively. Over time, a wide range of cell amplification was obtained in cultures with normal and thalassemic cells, depending on the individual blood donor from whom the cells had been derived. As a general feature, the cell number declined during the first week of culture, but increased thereafter to reach its maximal value between day 10 and day 15. In cultures of cells from normal donors (FIG. 3), the maximal cell number observed in culture ranged from values similar to the input to values approximately 80-fold higher. This variability appears to be due more to intrinsic properties of the cells used to start the cultures than to variability in the culture conditions, per se, since three separate cultures started with cells purified from the blood of the same donor gave very similar levels of amplification (FIG. 5). The cultures started with blood cells from the thalassemic patients behaved very similar to those obtained with normal donor cells. Also, in these cases, maximal amplification was observed between days 12 and 16. However, the magnitude of the amplification obtained in the thalassemic cultures was systematically lower than that observed in the normal ones (compare the average curve in the inset to FIG. 3 with that in the inset to FIG. 4). The morphology of the cells obtained at days 7 and 16 in representative proliferative-phase cultures of normal donors is presented in FIG. 6. Under light microscopic observation, the cultures contained a cell population homogeneous in size (panel I) that was composed of both erythroid and non-erythroid cells by day 7 (panel II), and almost completely of erythroid cells by day 16 (panel III). The differential counts on the smears obtained in two representative cultures are presented in FIGS. 7A and 7B. FIG. 7A presents the differentiation pattern most frequently observed: By day 7 the cells were almost entirely represented by immature erythroid cells, with some contamination by lymphoid or monocytic cells. As the culture progressed from day 7 to day 20, there was a progressive decline in the frequency of immature erythroid cells that was paralleled by an increase in the mature forms. No reticulocytes were observed in these cultures. In a minority of the cases, immature erythroid cells still represented the predominant cell population by day 10, but lymphocytes and monocytes persisted in the cultures and the frequency of monocytes, in particular, rose with time and made up about 20% of all the cells by day 17. In these cultures, reticulocytes were also detectable. However, because of their massive monocyte contamination, these cultures were discontinued after day 17. The progression of differentiation in the proliferative-phase culture was also documented by FACS analysis for the expression of the panleukocyte antigen CD45 and the erythroid-specific markers CD71 (transferring receptor) and glycophorin A. During erythroid differentiation, the cells lose CD45 expression. Alternatively, immature erythroid cells express high levels of CD71 (CD71$^{high}$) but no glycophorin A, while mature erythroid cells express medium levels of CD71 (CD71$^{medium}$) and glycophorin A (glycophorin A$^+$) (A. R. Migliaccio, et al., Disorders of Hemoglobin, 55 (2001)). As expected, the light-density cells of the blood expressed very few CD71$^+$ and glycophorin A$^+$ cells, and almost all the cells were CD45 (FIGS. 8, 9). By day 7 of the proliferative phase culture, almost all the cells were CD71$^{high}$, and very few were also glycophorin A$^+$. From day 12 to day 16, the frequency of glycophorin A$^+$ cells progressively increased, while the intensity of the CD71 expression decreased from high to medium (FIG. 8). At the same time, the number of cells expressing CD45 decreased and very few of them were still detectable by day 16 (FIGS. 8–10). In those cultures, the progression from a cell population CD71$^{high}$ glycophorin A$^{neg}$ (immature erythroblasts) to a population CD71$^{medium}$ glycophorin A$^+$ (mature erythroblasts) occurred in 9 days (from day 7 to day 16 of culture). The progression of the erythroid maturation in the proliferative phase and in the differentiative phase is compared in FIG. 10. This presents the FACS analysis for the coexpression of CD45/CD71 and of CD45/glycophorin A in cells kept in proliferation for 12 days or harvested from the proliferation phase at day 8 and induced to differentiate for 4 days with EPO and insulin. In the proliferative phase, nearly all the cells were losing CD45 expression by day 12 and two erythroid populations were clearly distinguished on the basis of their CD71 and glycophorin A expression: the majority of the cells were CD71$^{high}$ and glycophorin A$^{neg}$, and only a fraction of them were CD71$^{medium}$ and glycophorin A$^+$. In contrast, the cells transferred in EPO plus insulin had a homogeneous phenotype of CD45$^{neg}$/glycophorin A$^+$ and CD71$^{medium}$. Finally, in a last series of experiments it was evaluated how suitable these cells are for globin chain expression studies. Cells (3×10$^5$) from day 3 of the differentiation phase culture were incubated with [$^3$H]leucine and the proteins present in the cell lysate analyzed by HPLC. When the cells had been originated from light density cells purified from normal or thalassemic patients, a clean HPLC separation profile was observed with the radioactive peaks co-eluting with the major globin chains (FIG. 11). Since 10$^7$–10$^8$ erythroid cells can easily be obtained at the end of the differentiative phase cultures, this method allows the production of cells in numbers sufficient for at least 30 separate HPLC assays.

The foregoing detailed descriptions and examples have been given for clarity and understanding only. It will be appreciated by those skilled in the art that various modifications can the made to the above described embodiments of the invention without departing from the essential nature thereof. The invention is intended to encompass all such modifications within the scope of the appended claims.

What is claimed is:

1. A method of producing primary human erynthroid cells comprising the steps of:
   (i) obtaining light-density cells from a blood sample;
   (ii) culturing said light-density cells in a first culture medium comprising stem cell factor, erythropoietin, interleukin-3, dexamethasone and estradiol, thereby obtaining proliferation of the cells; and
   (iii) re-culturing said cells in a second culture medium comprising erythropoietin and human insulin, thereby obtaining differentiation of the cells into primary human erythroid cells.

2. The method according to claim 1, wherein said first culture medium is Iscove's modified Dulbecco's medium (IMDM) containing 20% of fetal bovine serum and said second culture medium is IMDM containing 20% of fetal calf serum.

3. The method according to claim 2, wherein said first culture medium comprises stem cell factor 10 ng/mL, erythropoietin 1 u/mL, interleukin-3 1 ng/mL, dexamethasone 10$^{-6}$ M and estradiol 10$^{-6}$ and said second culture medium comprises erythropoietin 1 u/mL and human insulin 10 ng/mL.

4. The method according to claim 3, wherein the cells are cultured in said culturing step for 8 to 14 days.

5. The method according to claim 4, wherein the cells are re-cultured in said re-culturing step for at least 4 days.

6. The method according to claim 1, further comprising washing the cells before said re-culturing step.

7. The method according to claim 6, wherein said first culture medium is IMDM containing 20% of fetal bovine serum and said second culture medium is IMDM containing 20% of fetal calf serum.

8. The method according to claim 7, wherein said first culture medium comprises stem cell factor 10 ng/mL, erythropoietin 1 u/mL, interleukin-3 1 ng/mL, dexamethasone 10$^{-6}$ M and estradiol 10$^{-6}$ and said second culture medium comprises erythropoietin 1 u/mL and human insulin 10 ng/mL.

9. The method according to claim 8, wherein the cells are cultured in said culturing step for 8 to 14 days.

10. The method according to claim 9, wherein the cells are re-cultured in said re-culturing step for at least 4 days.

* * * * *